United States Patent [19]

Jelley et al.

[11] Patent Number: 5,191,784
[45] Date of Patent: Mar. 9, 1993

[54] OPTO-ELECTRONIC GAS SENSOR

[75] Inventors: Kevin W. Jelley, Allentown, N.J.; G. J. Maclay, Maywood, Ill.

[73] Assignee: Siemens Corporate Research, Inc., Princeton, N.J.

[21] Appl. No.: 458,032

[22] Filed: Dec. 28, 1989

[51] Int. Cl.$^5$ .................. H01L 29/205; G01J 3/10
[52] U.S. Cl. .................. 73/31.06; 250/338.4; 25/15; 25/414
[58] Field of Search .................. 250/338.4; 357/30, 25, 357/4, 16; 73/31.06

[56]  References Cited

U.S. PATENT DOCUMENTS

| 4,348,686 | 9/1982 | Esaki et al. | 357/30 |
| 4,521,800 | 6/1985 | Howe | 357/42 |
| 4,581,621 | 4/1986 | Reed | 357/16 |
| 4,620,214 | 10/1986 | Margalit et al. | 357/16 |
| 4,731,338 | 3/1988 | Ralston et al. | 437/22 |
| 4,745,452 | 5/1988 | Sollner | 357/30 |
| 4,819,036 | 4/1989 | Kuroda et al. | 357/30 |
| 4,863,245 | 9/1989 | Roxlo | 357/16 |

FOREIGN PATENT DOCUMENTS 0275150 7/1988 European Pat. Off. .............. 357/16

OTHER PUBLICATIONS

Appl. Phys. Lett. 54(1), Jan. 2, 1989 "Dependence . . . Content" Kagawa et al., pp. 33-35.
"Tiny Electronic 'Noise' Promise Speedy Sensing", New York Times, Tuesday, Dec. 6, 1988.
"Quantum Well Makes New, High-Performance Optical Modulators", Thomas H. Wood, Laser Focus, Dec. 1986, pp. 121-124.
"Photocurrent response of GInAs/InP multiple quantum well detectors . . ", Temkin et al., Appl. Phys. Lett. 47(9), Nov. 1, 1985, pp. 978-980.
"A Dual-Mechanism Solid-State Carbon-Monoxide and Hydrogen Sensor . . . ", Jelley et al., IEEE Transactions on Electron Devices, vol. ED-34, No. Oct. 87, pp. 2086-2097.
"Well size related limitations on maximum electroabsorption in . . . ", Jelley et al., Appl. Phys. Lett. 55(1), Jul. 3, 1989, pp. 70-72.
"High-speed optical modulation with GaAs/GaAlAs quantum wells in a . . . ", Wood et al., Appl. Phys. Lett. 44(1), Jan. 1, 1984, pp. 16-18.
"Experimental Determination of Electroabsorption in . . . ", Jelley et al., Electronics Letter, Dec. 8, 1988, vol. 24, No. 25, pp. 1555-1557.
"High-contrast reflection modulation at normal incidence in asymmetric . . . ", Whitehead et al., Electronics Letters, Apr. 27, 1989, vol. 25, No. 9, pp. 568-568.

Primary Examiner—Jerome Jackson, Jr.
Attorney, Agent, or Firm—Adel A. Ahmed

[57]  ABSTRACT

Apparatus for detecting the presence of a gas in an ambient atmosphere comprises a multiple quantum well structure; a thin mesh of a transition metal formed on the multiple quantum well structure; and an arrangement for monitoring transmission of electromagnetic radiation through the mesh and the multiple quantum well structure.

6 Claims, 1 Drawing Sheet

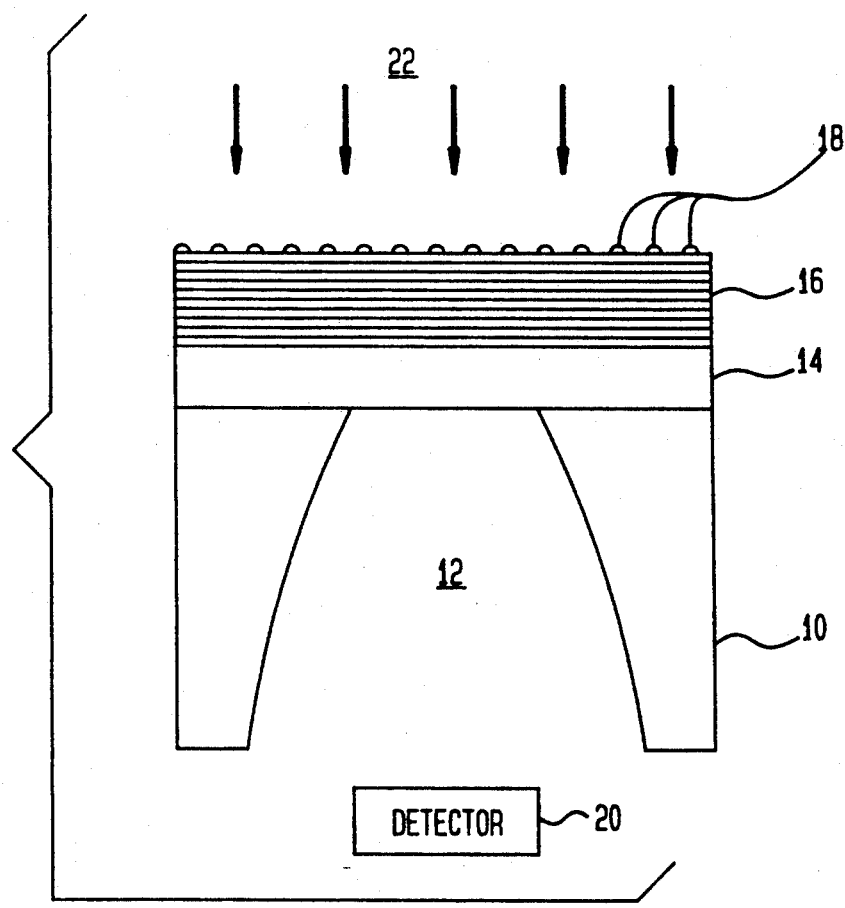
FIG. 1
FIG. 2
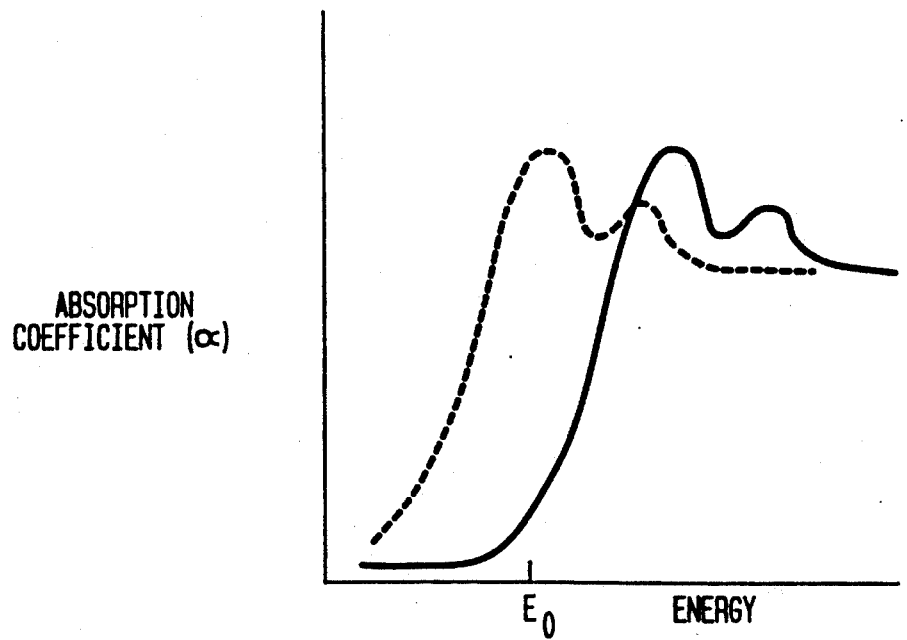
ABSORPTION COEFFICIENT ($\alpha$)
$E_0$  ENERGY

OPTO-ELECTRONIC GAS SENSOR

FIELD OF THE INVENTION

The present invention relates to sensors for gases and, more particularly, to semiconductor sensors for sensing the presence of particular gases in the ambient atmosphere, such as a hydrogen component gas.

DESCRIPTION OF THE RELATED ART

Sensors are known for detecting and signalling the presence of a gas by the effect of the gas on a semiconductor device. For example, a palladium-gate (Pd-gate) metal-oxide-semiconductor (MOS) structure sensitive to hydrogen gas is known. Such devices include a gate made of a transition metal, typically palladium in place of the conventional gate material generally utilized for an MOS device gate, such as aluminum or polysilicon. In a gas sensing device, the role of such a palladium gate structure is two-fold.

First, the gate acts as an electrode in contacting the device, and second, when exposed to hydrogen gas ($H_2$), gas, the palladium gate surface acts as a catalyst in the dissociation of molecular hydrogen into atomic hydrogen, which is then adsorbed on the Pd surface. Some of the atomic hydrogen will diffuse through the bulk palladium and be adsorbed at the interface of the palladium and the silicon dioxide ($SiO_2$), layer which typically is deposited under the gate electrode. The adsorbed hydrogen both at the surface and at the interface is polarized and forms a dipole layer. The dipole layer at the interface causes a shift in the threshold voltage ($V_T$) of the MOS structure. The magnitude of the threshold shift due to the dipole layer is approximately proportional to the density of dipoles at the interface, which in turn is related to the concentration of hydrogen in the gas. It is also believed that a change in bulk hydrogen concentration also causes a shift in the work function, which will shift the threshold voltage.

Other gases such as hydrogen sulfide and ammonia have been sensed with a Pd-gate MOS structure. Gases such as carbon monoxide are adsorbed on the palladium surface but are too large molecularly to diffuse through the palladium bulk and therefore, give no response. Response to carbon monoxide has been obtained using a modified Pd gate in which holes from 1.5 to 3.0 $\mu m$ in diameter have been patterned through the palladium to permit the carbon monoxide to reach the palladium-silicon dioxide interface.

In a further development, an ultra-thin palladium film has been deposited as an array of small individual islands separated from each other by a distance on the order of a few Å to about 100Å. The thickness of the film is kept below the point at which the islands tend to merge and, typically, may be in the order of 25Å. Electrical contact between the individual island globules occurs as a result of electron tunnelling. An account of the foregoing technology is provided, for example, in the article "A Dual-Mechanism Solid-State Carbon-Monoxide and Hydrogen Sensor Utilizing and Ultrathin Layer of Palladium", by Kevin W. Jelley and G. Jordan Maclay, IEEE Transactions on Electron Devices, Vol. ED-34, No. 10; October 1987.

Sensing of the shift in threshold voltage of the MOS device is typically performed by conventional electrical circuit arrangements. However, this requires connections to the MOS device, generally to the source and drain electrodes. It is herein recognized that the need for supply and sensing connections is a disadvantage, for example, in applications in which a sensor is located such that access has to be provided through gas-tight walls or glass windows.

SUMMARY OF THE INVENTION

In accordance with an aspect of the invention, apparatus for detecting the presence of a gas in an ambient atmosphere comprises a multiple quantum well structure or superlattice; a thin mesh of a transition metal formed on the multiple quantum well structure; and an arrangement for monitoring transmission of electromagnetic radiation through the mesh and the multiple quantum well structure.

In accordance with another aspect of the invention, a semiconductor device adapted for operation as a gas sensor comprises a body of a semiconductor material including a substrate region and including a multiple quantum well region over the substrate region. The superlattice region has first and second different materials arranged alternately in a plurality of parallel planar layers The planar layers exhibit an absorption edge for electromagnetic radiation at a first wavelength thereof and have a respective predetermined relatively thin thickness dimension of a value wherein an electric field acting perpendicularly to the planar layers causes the absorption edge to shift to a second wavelength of the electromagnetic radiation. A layer of a transition metal is formed over the superlattice region, the layer of transition metal having a relatively thin thickness dimension. The substrate region has at least a portion thereof removed for providing a clear passage for the electromagnetic radiation.

In accordance with still another aspect of the invention, the layer of transition metal is sufficiently thin as to be substantially transparent to the electromagnetic radiation.

In accordance with yet another aspect of the invention, the layer of transition metal is sufficiently thin as to be substantially permeable to a gas.

In accordance with a further aspect of the invention, the first material is aluminum gallium arsenide ($Al_xGaAs_{1-x}$) and the second material is gallium arsenide (GaAs).

In accordance with yet a further aspect of the invention, the layer of transition metal is of palladium.

In accordance with still a further aspect of the invention, the layer of a transition metal is formed on a final layer of the superlattice region, the final layer being of aluminum gallium arsenide.

BRIEF DESCRIPTION OF THE DRAWINGS

The invention will next be described in greater detail by way of an exemplatory embodiment and with the aid of the drawing in which FIG. 1 shows an embodiment of the invention, not to scale; and FIG. 2 is a graph, helpful in understanding the invention.

DETAILED DESCRIPTION OF THE PREFERRED EMBODIMENTS

Referring to FIG. 1, a gallium arsenide substrate 10 is doped at a level in the order of $10^{20} cm^{-3}$. Substrate 10 is opaque to electromagnetic radiation in the wavelength range of interest which is in the vicinity of 850 nanometers. Accordingly, a portion of substrate 10 is removed by etching so as to leave free a passage, generally indicated by reference numeral 12, around the center axis open for free passage of electromagnetic radiation, including light rays. Substrate 10 has formed thereon a region 14 of AlGaAs doped slightly less than the substrate, $10^{18}$ cm$^{-3}$. An undoped multiquantum well structure (MQW) 16 is formed over region 14. MQW 16 comprises a plurality of alternating layers of GaAs and AlGaAs, the layers being each in the order of 100 Å thick. A thin layer of a transition metal which may be palladium is formed over the topmost layer of MQW 16. Preferrably, this topmost layer of MQW 16 is of AlGaAs, although this is not essential. The thickness of the layer of palladium is preferably in the order of 50 Å. It is herein recognized that a palladium layer of such thin dimensions is typically discontinuous and on a microscopic scale comprises a mesh or matrix-like spread of individual islands. The layer of palladium is thus indicated schematically in FIG. 1 as a series of dots 18. A light detector 20 is located in the clear path provided through the substrate so as to detect any light that is transmitted from a source above layer 18 through layer 18 and region 12. Light or other electromagnetic radiation incident on layer 18 is schematically shown in FIG. 1 as a series of arrows 22 emanating from a source not shown.

The characteristics of multiple quantum well structures such as MQW 16 are known. See the above referenced paper and, for example, the technical articles "Well size related limitations on maximum eletroabsorption in GaAs/AlGaAs multiple quantum well structures", K.W. Jelley et al., Appl. Phys. Lett. 55(1), Jul. 3, 1989; pp70–72; "High-speed optical modulation with GaAs/AlGaAs quantum wells in p-i-n diode structure", T.H. Wood et al., Appl. Phys. Lett. 44(1), Jan. 1, 1984; "Experimental determination of electroabsorption in GaAs/Al$_{0.32}$Ga$_{0.68}$As multiple quantum well structures as function of well width", K.W. Jelley et al., Electronics Letters, Dec. 8, 1988, Vol. 24 No. 25 pp 1555–1557; "High-contrast reflection modulation at normal incidence in asymmetric multiple quantum well Fabry-Perot structure", M. Whitehead et al., Electronics Letters, Apr. 27, 1989, Vol. 25 No. 9, pp 566–568; and U.S. Pat. No. 4,731,338 (Ralston et al.), herein incorporated by reference.

Briefly, it is known that GaAs/AlGaAs quantum wells experience a shift to longer wavelengths in their absorption edge when acted upon by a perpendicular electric field. This is indicated schematically in FIG. 2 in which the solid line indicates the absorption coefficient without the presence of an electric field and the dashed line indicates the absorption coefficient under the action of an electric field.

In operation, light is transmitted through the structure, as described so as to impinge on detector 20. A wavelength somewhat longer than 850 nanometers is selected so as to be passed by the GaAs well whose absorption edge is at about 850 nanometers. Palladium layer 18 is then exposed to an atmosphere in which hydrogen may be present which it is desired to detect.

As has been earlier mentioned, it is known that when exposed to hydrogen gas (H$_2$), gas, the palladium surface acts as a catalyst in the dissociation of molecular hydrogen into atomic hydrogen, which is then adsorbed on the Pd surface. Some of the atomic hydrogen will diffuse through the interstices in the palladium mesh and be adsorbed at the surface of the topmost layer of MQW 16. The adsorbed hydrogen at the surface is polarized and forms a dipole layer. The dipole layer at the surface results in the effect of a bias being applied to palladium layer 18, which causes an electric field to act on MQW 16. The high level of doping in layer 14 and in substrate 10 will tend to restrict the resulting electric field to MQW 16 and thus maximize its effect. The electric field then causes the absorption edge to shift to a longer wavelength, as indicated in FIG. 2.

If the transmitted light being monitored is of the correct wavelength, it will now fall within the shifted absorption edge and detector 20 will register a drop in intensity and thereby indicate the presence of hydrogen. Naturally, the greater the concentration of hydrogen in the atmosphere to which the layer 18 is exposed, the greater the shift, so that the extent to which light is absorbed or transmitted provides a quantitative measure of the concentration of hydrogen in the ambient atmosphere.

The invention has been described by way of an illustrative embodiment. Various changes are possible which will be apparent to one skilled in the art. For example, other materials can be used for the detection of other gases and to allow operation at other wavelengths. For another example, light can be transmitted in either direction for monitoring of the absorption edge change. Such and similar changes and modifications do not depart from the spirit and scope of the invention which is intended to be limited only by the claims following.

We claim:

1. A semiconductor device adapted for operation as a gas sensor, comprising:

a body of semiconductor material including a substrate region and a multiple quantum well (MQW) structure over said substrate region, said MQW structure having first and second different materials arranged alternately in a plurality of parallel planar layers in a vertical direction, said planar layers exhibiting an absorption edge for electromagnetic radiation at a first wavelength thereof and having a respective predetermined relatively thin thickness dimension of a value wherein an electric field acting perpendicularly to said planar layers causes a shifting of said absorption edge from said first wavelength of said electromagnetic radiation to a second wavelength of said electromagnetic radiation;

a layer of a transition metal formed over a topmost layer of said MQW structure, said layer of a transition metal having a relatively thin thickness dimension being substantially transparent to the electromagnetic radiation and substantially permeable to a gas to be detected; and a light detector, located below said substrate region, for detecting the sifting in wavelength of said electromagnetic radiation transmitted in the vertical direction through said layer of transition metal, said MQW structure, and said substrate region, wherein said layer of transition metal allows gas atoms to permeate into the topmost layer of said MQW structure so as to form a dipole layer resulting in an electric field acting perpendicularly to said planar layers of said MQW structure, thereby causing a shifting in wavelength of said electromagnetic radiation which is detected by said light detector to indicate the presence of the gas.

2. A semiconductor device as recited in claim 1, wherein said first material is aluminum gallium arsenide ($Al_xGaAs_{1-x}$) and said second material is gallium arsenide (GaAs).

3. A semiconductor device as recited in claim 2, wherein said layer of a transition metal is of palladium.

4. A semiconductor device as recited in claim 1, wherein said substrate region is made of an optically opaque material and has at least a portion thereof removed for providing a clear passage for said electromagnetic radiation, and said light detector is located in said passage.

5. A semiconductor device as recited in claim 3, wherein said substrate region is made of an optically opaque material and has at least a portion thereof removed for providing a clear passage for said electromagnetic radiation, and said light detector is located in said passage.

6. A semiconductor device as recited in claim 3, wherein said topmost layer of said MQW structure is made of aluminum gallium arsenide.

* * * * *